United States Patent [19]

Traub

[11] Patent Number: 4,730,646
[45] Date of Patent: Mar. 15, 1988

[54] METHOD FOR CONTROLLING PROPER INFLATION OF ATHLETIC BALLS

[75] Inventor: Barry H. Traub, Dunwoody, Ga.

[73] Assignee: Select Service & Supply Co., Inc., Atlanta, Ga.

[21] Appl. No.: 897,839

[22] Filed: Aug. 19, 1986

[51] Int. Cl.⁴ .............................................. A63B 41/12
[52] U.S. Cl. ...................... 141/4; 273/58 B
[58] Field of Search ...................... 53/79, 84, 85, 403, 53/503; 141/4, 5; 33/179; 273/61 D, 58 R, 58 B

[56] References Cited

U.S. PATENT DOCUMENTS

| | | | |
|---|---|---|---|
| 105,895 | 8/1870 | Bonham | 33/176 |
| 483,642 | 10/1892 | Behmer | 33/176 |
| 1,572,193 | 2/1926 | Engel | 33/179 |
| 1,854,860 | 4/1932 | Osborn | 33/179 |
| 2,205,626 | 6/1940 | Mason | 33/179 |
| 2,262,664 | 11/1941 | Bresson | 33/179 |
| 2,989,050 | 6/1961 | Mayo et al. | 33/179 X |
| 3,932,977 | 1/1976 | Ringler | 141/4 X |
| 4,433,486 | 2/1984 | Muehlenbein | 33/137 R |
| 4,441,258 | 4/1984 | McDaniel et al. | 33/179 |
| 4,459,754 | 7/1984 | Yasuda et al. | 33/137 R |
| 4,473,949 | 10/1984 | Schechtman | 33/141 E |

Primary Examiner—Mark J. Thronson
Attorney, Agent, or Firm—Browdy and Neimark

[57] ABSTRACT

The proper inflation of playground balls is controlled by fixing a strap to a predetermined circumference equal to the circumference of the ball at proper inflation. The strap is then placed around the center of the ball and the ball inflated until the strap is tight. The strap is then removed and the ball is properly inflated. The strap may be secured at any of a plurality of settings equal to the circumference at proper inflation of any of a plurality of different balls. The strap is marked with numbers equal to the diameter at proper inflation of the ball to be inflated. The desired circumference of the strap is preferably maintained with a hook-and-pile type fastener.

8 Claims, 3 Drawing Figures

METHOD FOR CONTROLLING PROPER INFLATION OF ATHLETIC BALLS

FIELD OF THE INVENTION

The present invention relates to a device and a method for controlling the proper inflation of athletic balls and, more particularly, to a strap and a method for using such a strap with which balls can be inflated exactly to a desired diameter.

BACKGROUND OF THE INVENTION

Playground balls are rubber balls which are soft and pliable because they have no carcass, i.e., no nylon-wound bladder. Playground balls are primarily used for bouncing, catching and bombardment-type activities. They are widely used by schools, recreation facilities and physical therapists. Playground balls are specifically designed for inflation to a particular diameter. Individual playground balls which are specifically designed for each of four, five, six, seven, eight and one-half, ten, thirteen and sixteen inch inflation, are common.

Because playground balls have no nylon wound bladder there is nothing to stop them from being over-inflated and it is very common that playground balls become over-inflated. When a playground ball is over-inflated, the seams tend to spread and the lifetime of the ball is drastically reduced. Severe over-inflation could even cause explosion of the ball upon impact which, of course, is not very desirable among young children. Under-inflation is also a problem as unless fully inflated the ball will not bounce correctly.

Achieving proper inflation of a playground ball has been a major difficulty to the present time. Generally, the problem is ignored, resulting in common over-inflation and substantial diminishment of the life of playground balls. Even when the problem is not ignored, the amount of inflation can only be roughly estimated, perhaps by placing the ball upon a ruler and looking at it from above in order to estimate the diameter to which it has been inflated. This is very difficult and inaccurate. No device is presently on the market which addresses this problem.

SUMMARY OF THE INVENTION

Accordingly it is an object of the present invention to solve the problems of the prior art.

It is another object of the present invention to provide a device with which playground balls can be inflated exactly to their rated diameter.

It is still another object of the present invention to provide a strap which can be set to any of a plurality of desired diameters.

It is yet another object of the present invention to provide such a strap made of hook-and-pile material so as to be self adhering.

It is a further object of the present invention to provide a process for controlling the desired inflation of playground balls.

These and other objects are accomplished in accordance with the present invention which comprises a strap having self adhering hook-and-pile material on one side thereof and clear markings on the other side thereof specifying the diameter of the ball which will be encompassed by the strap when secured into a loop set to the marked diameter. The strap is set to one of the marked diameters, placed around the playground ball prior to inflation and the ball is then inflated until the strap is tight. When removed, the ball is correctly inflated and the strap is ready to use again.

DESCRIPTION OF PREFERRED EMBODIMENTS

Figure 1:
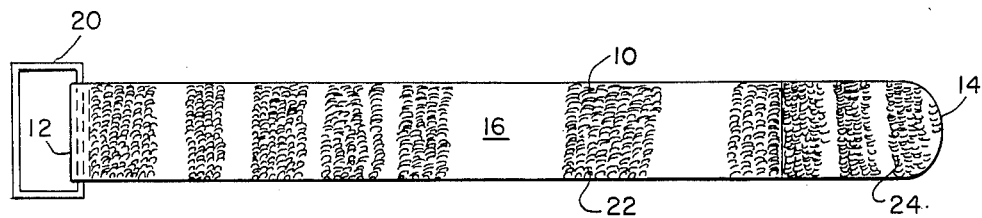
FIG. 1 is a plan view showing one side of a strap in accordance with the present invention.
Figure 2:
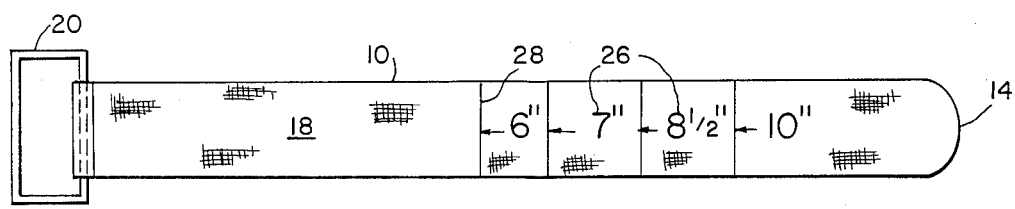
FIG. 2 is a plan view showing the opposite side of a strap in accordance with the present invention.

FIG. 1 shows a strap 10 in accordance with the present invention having a first end 12 and a second end 14. Surface 16 of the strap 10 is shown in FIG. 1, while surface 18, which is the underside of surface 16, is shown in FIG. 2. At the first end 12 of the strap 10, a rigid ring or loop 20 is connected to the strap. The ring 20 may be made of any rigid material as for example a rigid plastic or metal.

Surface 16 of strap 10 is covered over nearly its entire length with the pile or loop portion 22 of a hook-and-pile fastener such as that sold under the trademark VELCRO. The tip of the strap near the end 14 is covered with the hook portion 24 of the hook-and-pile fastener. Thus, the end of the strap containing hook portion 24 may be folded back and fastened to any portion of the remainder of the strap 10 bearing the pile portion 22 in order to form a strap of any of varying lengths.

On the opposite side 18 of the strap 10, lines 28 and numbers 26 are marked on the strap 10. The markings are not numbers which correspond to the length of the strap (or circumference of the strap if formed into a loop), but equal the diameter of the loop which would be formed by passing the end 14 of the strap through the ring 20 up to the associated line 28. Thus, for example, the line 28 marked "6" inches is disposed pi×6 inches from the end of the loop 20 or 18.84 inches therefrom. The same is true for the other lines 28.

Figure 3:
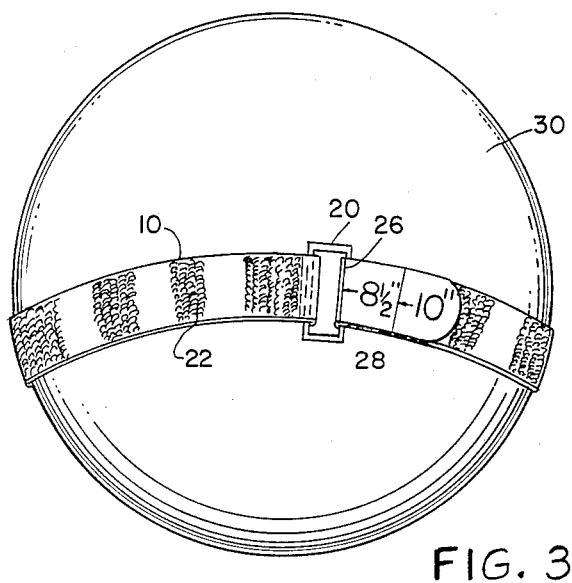
FIG. 3 is a perspective view of a strap in accordance with the present invention when in use encircling a ball which has been inflated up to the diameter indicated on the strap.

In use, the end 14 of the strap 10 is passed through the ring 20 in such a manner that the strap forms a loop with the surface 18 on the interior of the loop, and the surface 16 on the exterior of the loop with the free end 14 of the strap passing through the ring 20 in a direction which is directed outside of the loop formed by the strap 10. The tip 14, after passing through the ring 20, reverses direction and is continued to be pulled until the correct diameter marking 26 on the surface 18 of the strap 10 lines up with the ring 20. As shown in FIG. 3, the eight and one-half inch marking lines up with the ring 20. Once the proper alignment is made, the hook portion 24 of the hook-and-pile fastener at the tip 14 of the strap 10 is pressed against the fuzzy pile material 22. It will adhere automatically, thus securing the strap into a loop of the desired diameter. The strap 10 is now set at the correct circumference for the diameter ball shown by the indicia 26.

Once the strap is set to the correct diameter of the ball to be inflated in the manner discussed hereinabove, the strap is placed around the ball 30 at its center. The center of the ball 30 can usually be identified by the center seam thereof, not shown. The ball is then inflated until the strap 10 is tight, as shown in FIG. 3. The strap tip 14 may then be disengaged by pulling upward and the strap removed from the ball 30. The ball 30 is now inflated to its rated diameter and is ready to be played with.

The strap 10 may be made of any desired flexible material which has no substantial extensibility in the longitudinal direction, such as nylon or leather.

The preferred embodiment of the present invention utilizes a hook-and-pile type fastener, as this is ideally suited for the utility in which the present strap is used. It is infinitely adjustable, within certain end limits, and is quickly and easily fastened to an appropriate diameter and unfastened. However, other securing means can be used in accordance with the present invention. For example, other pressure-locking fastening means can be used as a substitute for the hook-and-pile type fastener, such as, for example, a low tack pressure sensitive adhesive. Furthermore, a conventional belt buckle may be used with the punch holes for the buckle prong being disposed at appropriate intervals to provide the desired diameters when buckled to those punch holes and with the number indications being marked on the outer surface of the belt in conjunction with each of the punch holes. Again, the indications are a measure of inches of diameter of the ball to be inflated at the particular circumference, not an indication of the length of the belt or the circumference thereof when buckled. Any other type of fastening means may similarly be used.

Rather than being marked with an indicia equal to the diameter of the ball, the inflation of which is to be controlled by the strap, the markings thereon may otherwise identify the ball. For example, if a six inch playground ball is commonly referred to as a "junior" ball, for example, or if each of the different sizes are identified by different colors, the marks 26 on the strap 10 may identify the balls by words such as "junior", "soccer", "volleyball", etc., or by colors such as "red", "yellow", etc. The markings 26, however, should never equal the length or circumference of the strap, as such numbers would be meaningless when dealing with playground balls.

In order to cover all of the common sizes of playground balls from four inches through sixteen inches, it is necessary to sell the straps in accordance with the present invention in groups of three straps, each having a different length. The longest straps, of course, being used with the larger balls and the smaller straps being used for the smaller balls.

While the strap and method of the present invention are preferably used to control the inflation of playground balls, they can theoretically be used to control the inflation of other inflatable objects, preferably having at least one cross-section which is round. For example, the inflation of an inner tube could be controlled by placing the strap around the arm of the tube.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method for obtaining proper inflation of an inflatable athletic ball having predetermined dimensions at proper inflation, using a flexible strap having a length greater than the circumference of the object at proper inflation and having securing means for securing the ends of the strap to one another so as to form a continuous configuration the circumference of which can be set to any of a plurality of predetermined lengths corresponding to the dimensions at proper inflation of a plurality of different inflatable balls, comprising:

setting the securing means of the strap to a circumference corresponding to the predetermined dimension at proper inflation of the ball to be inflated;

placing the strap around the ball to be inflated;

inflating the ball until further inflation is limited by the strap; and discontinuing inflation and removing the ball from the strap.

2. A method in accordance with claim 1, wherein the strap being used further includes indicator means for displaying an indicia representative of the size of the ball at proper inflation at each setting of the securing means and wherein said setting step comprises setting the securing means to the setting at which the indicator means displays an indica representative of the size of the ball to be inflated when at proper inflation.

3. A method in accordance with claim 1, wherein the inflatable ball is spherical when at proper inflation.

4. A method in accordance with claim 2, wherein the inflatable ball is spherical when at proper inflation and wherein each said indicia displayed by the indicator means is a number which is equal to the diameter of one of a plurality of different balls at proper inflation and wherein said setting step comprises setting the securing means to the setting at which the indicator means displays the diameter at proper inflation of the ball to be inflated.

5. A method in accordance with claim 1, wherein the strap includes a rigid ring connected to one end thereof and the securing means comprises a pressure-locking fastening means on one surface of the strap, and wherein said setting step comprises passing the end of the strap opposite to the ring through the ring in a direction in which the end opposite the ring is directed outside of the loop thereby formed by the strap, and pulling the strap through the ring until the desired circumference length is reached and folding the free end of the strap back about the ring until it comes into engagement with the remainder of the strap, and applying pressure to the overlapping portion of the strap to cause the pressure-locking fastening means to lock the strap into the desired circumference.

6. A method in accordance with claim 5, wherein the strap being used further includes indicator means for displaying an indicia representative of the size of the ball at proper inflation at each setting of the securing means and wherein said setting step comprises setting the securing means to the setting at which the indicator means displays an indicia representative of the size of the ball to be inflated when at proper inflation.

7. A method in accordance with claim 6, wherein said indicator means comprises numbers marked on the surface of the strap opposite the surface bearing the pressure-locking fastening means.

8. A method in accordance with claim 5, wherein said pressure-locking fastening means comprises a hook-and-pile fastener, one of the hook-and-pile portions of said fastener being disposed only at the end of the strap opposite the ring and the other portion of the fastener covering substantially the entire remainder of the surface of the strap bearing the fastening means.

* * * * *